US007977288B2

(12) United States Patent
SenGupta

(10) Patent No.: US 7,977,288 B2
(45) Date of Patent: Jul. 12, 2011

(54) COMPOSITIONS CONTAINING CATIONICALLY SURFACE-MODIFIED MICROPARTICULATE CARRIER FOR BENEFIT AGENTS

(75) Inventor: Ashoke K. SenGupta, Barrington, IL (US)

(73) Assignee: Amcol International Corporation, Hoffman Estates, IL (US)

( * ) Notice: Subject to any disclaimer, the term of this patent is extended or adjusted under 35 U.S.C. 154(b) by 191 days.

(21) Appl. No.: 12/397,043

(22) Filed: Mar. 3, 2009

(65) Prior Publication Data

US 2009/0162408 A1 Jun. 25, 2009

Related U.S. Application Data

(63) Continuation-in-part of application No. 12/028,685, filed on Feb. 8, 2008, now Pat. No. 7,915,214, which is a continuation-in-part of application No. 11/331,248, filed on Jan. 12, 2006, now Pat. No. 7,569,533.

(60) Provisional application No. 60/643,430, filed on Jan. 12, 2005.

(51) Int. Cl.
*C11D 3/37* (2006.01)

(52) U.S. Cl. ........ 510/122; 510/119; 510/130; 510/135; 510/136; 510/466

(58) Field of Classification Search .................. 510/119, 510/122, 130, 135, 136, 466
See application file for complete search history.

(56) References Cited

U.S. PATENT DOCUMENTS

| 2,800,457 | A | 7/1957 | Green et al. |
|---|---|---|---|
| 3,041,288 | A | 6/1962 | Anthony |
| 3,415,758 | A | 12/1968 | Powell et al. |
| 3,516,941 | A | 6/1970 | Matson |
| 3,723,325 | A | 3/1973 | Parran |
| 3,870,542 | A | 3/1975 | Ida et al. |
| 4,145,184 | A | 3/1979 | Brain et al. |
| 4,152,272 | A | 5/1979 | Young |
| 4,318,818 | A | 3/1982 | Letton et al. |
| 4,387,090 | A | 6/1983 | Bolich, Jr. |
| 4,402,856 | A | 9/1983 | Schnoring et al. |
| 4,424,134 | A | 1/1984 | Sissin et al. |
| 4,446,032 | A | 5/1984 | Munteanu et al. |
| 4,446,042 | A | 5/1984 | Leslie |
| 4,464,271 | A | 8/1984 | Munteanu et al. |
| 4,515,705 | A | 5/1985 | Moeddel |
| 4,534,891 | A | 8/1985 | Boden et al. |
| 4,537,706 | A | 8/1985 | Severson, Jr. |
| 4,537,707 | A | 8/1985 | Severson, Jr. |
| 4,550,862 | A | 11/1985 | Barker et al. |
| 4,561,998 | A | 12/1985 | Wertz et al. |
| 4,597,898 | A | 7/1986 | Vander Meer |
| 4,664,064 | A | 5/1987 | Lowe |
| 4,673,568 | A | 6/1987 | Grollier et al. |
| 4,690,825 | A | 9/1987 | Won |
| 4,705,681 | A | 11/1987 | Maes et al. |
| 4,710,374 | A | 12/1987 | Grollier et al. |
| 4,714,562 | A | 12/1987 | Roselle et al. |
| 4,767,547 | A | 8/1988 | Straathof et al. |
| 4,842,849 | A | 6/1989 | Grollier et al. |
| 4,946,624 | A | 8/1990 | Michael |
| 4,948,818 | A | 8/1990 | Carmody et al. |
| 4,954,285 | A | 9/1990 | Wierenga et al. |
| 4,962,133 | A | 10/1990 | Chromecek et al. |
| 4,962,170 | A | 10/1990 | Chromecek et al. |
| RE33,429 | E | 11/1990 | Abrutyn |
| 4,968,451 | A | 11/1990 | Scheibel et al. |
| 4,973,422 | A | 11/1990 | Schmidt |
| 5,085,857 | A | 2/1992 | Reid et al. |
| 5,112,688 | A | 5/1992 | Michael |
| 5,126,061 | A | 6/1992 | Michael |
| 5,137,646 | A | 8/1992 | Schmidt et al. |
| 5,145,842 | A | 9/1992 | Driedger et al. |
| 5,169,552 | A | 12/1992 | Wise |
| 5,194,639 | A | 3/1993 | Connor et al. |
| 5,207,998 | A | 5/1993 | Robinson et al. |
| 5,275,755 | A | 1/1994 | Sebag et al. |
| 5,288,417 | A | 2/1994 | Bauer et al. |
| 5,288,431 | A | 2/1994 | Huber et al. |
| 5,306,434 | A | 4/1994 | Schueller et al. |
| 5,403,499 | A | 4/1995 | Kiefer et al. |
| 5,411,671 | A | 5/1995 | Bauer et al. |

(Continued)

FOREIGN PATENT DOCUMENTS

WO WO-9811869 3/1998

(Continued)

OTHER PUBLICATIONS

PCT International Search Report and Written Opinion; International Application No. PCT/US2009/035871; International Filing Date Mar. 3, 2009.

International Search Report for International application No. PCT/US2006/001019 (Jun. 7, 2006) by the European Patent Office (2 pages).

Poucher, W.A. Perfumes Cosmetics and Soaps. Second Edition. 1959.

International Preliminary Report of Patentability for International Application No. PCT/US2006/001019 (Jul. 17, 2007) by The International Bureau of WIPO (7 pages).

(Continued)

*Primary Examiner* — Charles I Boyer
(74) *Attorney, Agent, or Firm* — Marshall, Gerstein & Borun LLP

(57) ABSTRACT

A coated microparticulate composition comprising a microparticulate; wherein the microparticulate comprises a benefit agent; and wherein the microparticulate is coated with: a Type-1 Polymer, wherein the Type-1 Polymer comprises a cationic polymer with a cationic atom content greater than about 3 wt. % and a weight average molecular weight less than about 800,000 Dalton; and a Type-2 Polymer, wherein the Type-2 Polymer comprises a cationic polymer with a cationic atom content less than about 3 wt. % and a weight average molecular weight greater than about 1,000,000 Dalton.

34 Claims, No Drawings

U.S. PATENT DOCUMENTS

| | | | |
|---|---|---|---|
| 5,458,809 A | 10/1995 | Fredj et al. | |
| 5,458,810 A | 10/1995 | Fredj et al. | |
| 5,460,752 A | 10/1995 | Fredj et al. | |
| 5,466,802 A | 11/1995 | Panandiker et al. | |
| 5,470,507 A | 11/1995 | Fredj et al. | |
| 5,500,152 A | 3/1996 | Helliwell et al. | |
| 5,543,074 A | 8/1996 | Hague et al. | |
| 5,545,340 A | 8/1996 | Wahl et al. | |
| 5,545,350 A | 8/1996 | Baker et al. | |
| 5,559,261 A | 9/1996 | Sivik | |
| 5,562,849 A | 10/1996 | Wahl et al. | |
| 5,565,145 A | 10/1996 | Watson et al. | |
| 5,574,179 A | 11/1996 | Wahl et al. | |
| 5,581,005 A | 12/1996 | Perkins | |
| 5,597,936 A | 1/1997 | Perkins et al. | |
| 5,618,523 A | 4/1997 | Zysman et al. | |
| 5,661,118 A | 8/1997 | Cauwet et al. | |
| 5,674,832 A | 10/1997 | Keys | |
| 5,677,407 A | 10/1997 | Sojka | |
| 5,679,630 A | 10/1997 | Baeck et al. | |
| 5,703,030 A | 12/1997 | Perkins et al. | |
| 5,703,034 A | 12/1997 | Offshack et al. | |
| 5,705,464 A | 1/1998 | Scheper et al. | |
| 5,712,358 A | 1/1998 | Sojka | |
| 5,726,138 A | 3/1998 | Tsaur et al. | |
| 5,731,278 A | 3/1998 | Nair et al. | |
| 5,756,436 A | 5/1998 | Royce et al. | |
| 5,759,990 A | 6/1998 | Wahl et al. | |
| 5,776,443 A | 7/1998 | Vinski et al. | |
| 5,777,054 A | 7/1998 | Sojka | |
| 5,830,960 A | 11/1998 | Sojka | |
| 5,830,967 A | 11/1998 | Sojka | |
| 5,834,577 A | 11/1998 | Sojka | |
| 5,837,661 A | 11/1998 | Evans et al. | |
| 5,837,790 A | 11/1998 | Sojka | |
| 5,853,707 A | 12/1998 | Wells et al. | |
| 5,877,145 A | 3/1999 | Wahl et al. | |
| 5,902,781 A | 5/1999 | Painter | |
| 5,914,101 A | 6/1999 | Tapley et al. | |
| 5,914,307 A | 6/1999 | DeNome et al. | |
| 5,916,862 A | 6/1999 | Morelli et al. | |
| 5,923,203 A | 7/1999 | Chen et al. | |
| 5,929,022 A | 7/1999 | Velazquez | |
| 5,932,203 A | 8/1999 | Coffindaffer et al. | |
| 5,935,561 A | 8/1999 | Inman et al. | |
| 5,939,373 A | 8/1999 | Haeggberg et al. | |
| 5,955,552 A | 9/1999 | Sojka | |
| 5,962,386 A | 10/1999 | Scheper et al. | |
| 5,968,286 A | 10/1999 | Crudele et al. | |
| 5,968,881 A | 10/1999 | Haeggberg et al. | |
| 5,985,295 A * | 11/1999 | Peffly | 424/401 |
| 5,990,059 A | 11/1999 | Finel et al. | |
| 5,990,065 A | 11/1999 | Vinson et al. | |
| 5,997,886 A * | 12/1999 | Peffly et al. | 424/401 |
| 6,017,871 A | 1/2000 | Baeck et al. | |
| 6,020,294 A | 2/2000 | Getty et al. | |
| 6,024,943 A | 2/2000 | Ness et al. | |
| 6,051,540 A | 4/2000 | Shefer et al. | |
| 6,069,122 A | 5/2000 | Vinson et al. | |
| 6,107,429 A | 8/2000 | Sojka | |
| 6,126,954 A | 10/2000 | Tsaur | |
| 6,149,898 A * | 11/2000 | Peffly et al. | 424/70.12 |
| 6,156,713 A | 12/2000 | Chopra et al. | |
| 6,162,423 A | 12/2000 | Sebag et al. | |
| 6,248,849 B1 | 6/2001 | Sojka | |
| 6,261,483 B1 | 7/2001 | Frank et al. | |
| 6,277,361 B1 | 8/2001 | Murray et al. | |
| 6,329,057 B1 | 12/2001 | Dungworth et al. | |
| 6,335,315 B1 | 1/2002 | Trinh et al. | |
| 6,387,995 B1 | 5/2002 | Sojka | |
| 6,436,383 B2 | 8/2002 | Murray et al. | |
| 6,541,565 B2 | 4/2003 | Hood et al. | |
| 6,667,029 B2 | 12/2003 | Zhong et al. | |
| 6,706,258 B1 | 3/2004 | Gallagher et al. | |
| 6,740,631 B2 | 5/2004 | Shefer et al. | |
| 6,790,814 B1 | 9/2004 | Marin et al. | |
| 6,844,302 B1 | 1/2005 | Boden et al. | |
| 7,026,308 B1 * | 4/2006 | Gavin et al. | 514/188 |
| 7,118,057 B2 | 10/2006 | Hao et al. | |
| 7,119,057 B2 | 10/2006 | Popplewell et al. | |
| 7,119,060 B2 | 10/2006 | Shefer et al. | |
| 7,122,512 B2 | 10/2006 | Brain et al. | |
| 7,125,835 B2 | 10/2006 | Bennett et al. | |
| 7,196,049 B2 | 3/2007 | Brain et al. | |
| 7,294,612 B2 | 11/2007 | Popplewell et al. | |
| 2003/0049282 A1 | 3/2003 | Aronson et al. | |
| 2003/0224954 A1 | 12/2003 | Wells et al. | |
| 2005/0158266 A1 | 7/2005 | Peffly et al. | |
| 2005/0227907 A1 | 10/2005 | Lee | |
| 2005/0277568 A1* | 12/2005 | Keenan et al. | 510/438 |
| 2006/0014655 A1 | 1/2006 | Smets | |
| 2006/0094628 A1* | 5/2006 | Wei et al. | 510/417 |
| 2006/0281650 A1* | 12/2006 | Keenan et al. | 510/141 |
| 2007/0077221 A1* | 4/2007 | Seigneurin et al. | 424/70.16 |
| 2007/0280976 A1* | 12/2007 | Taylor et al. | 424/401 |
| 2007/0293411 A1* | 12/2007 | Focht et al. | 510/158 |
| 2008/0139432 A1* | 6/2008 | Peffly et al. | 510/122 |
| 2008/0206179 A1* | 8/2008 | Peffly et al. | 424/70.13 |
| 2009/0005460 A1* | 1/2009 | Gunn et al. | 514/727 |
| 2009/0156563 A1* | 6/2009 | Baschong et al. | 514/159 |
| 2009/0214447 A1* | 8/2009 | Jennings et al. | 424/49 |

FOREIGN PATENT DOCUMENTS

| | | |
|---|---|---|
| WO | WO-9811870 | 3/1998 |
| WO | WO-0174310 A2 | 10/2001 |

OTHER PUBLICATIONS

International Search Report for International Application No. PCT/US2008/006138 (Oct. 31, 2008) by The Korean Intellectual Property Office (2 pages).

* cited by examiner

COMPOSITIONS CONTAINING CATIONICALLY SURFACE-MODIFIED MICROPARTICULATE CARRIER FOR BENEFIT AGENTS

CROSS-REFERENCE TO RELATED APPLICATIONS

This application claims the benefit of the filing dates of U.S. patent application Ser. No. 12/028,685, filed Feb. 8, 2008, which is a continuation-in-part of U.S. patent application Ser. No. 11/331,248, filed Jan. 12, 2006, which claims the benefit of U.S. Provisional Pat. Appl. No. 60/643,430, filed Jan. 12, 2005; Ser. No. 12/152,364, filed May 14, 2008, which is a continuation-in-part of U.S. patent application Ser. No. 11/331,248; Ser. No. 12/327,570, filed Dec. 3, 2008, which is a continuation-in-part of U.S. patent application Ser. Nos. 12/152,364, 12/028,685, and 11/331,248; U.S. Provisional Patent Application Nos. 61/044,381, filed Apr. 11, 2008; and 61/101,336, filed Sep. 30, 2008, each incorporated herein by reference in their entirety.

FIELD OF THE INVENTION

The present invention is directed to carrier materials containing one or more benefit agents, e.g., a liquid fragrance, that have increased deposition onto substrates as a result of a plurality of cationic coating materials.

BACKGROUND OF THE INVENTION

The consumer products industry has long searched for ways to enhance the performance of fabric care products, like a fabric softener, and to make the products more esthetically pleasing to consumers. For example, fragrance is an important ingredient in successful commercial fabric care products because, in addition to imparting an esthetically pleasing odor, a fragrance conveys a positive image of product performance to the consumer, e.g., the fabric is clean and fresh.

Fragrances typically are added to fabric care products to provide a fresh, clean impression for the product itself, as well as to the fabric treated with the product. Although the fragrance does not enhance the performance of a fabric care product, the fragrance makes these products more esthetically pleasing, and consumers expect and demand a pleasing odor for such products.

A fragrance plays an important, and often a determining, role when the consumer selects and purchases a fabric care product. Many consumers desire the fragrance to be deposited on the fabric and remain on the fabric for an extended time in order to convey a continuing impression of freshness. Consumers also desire fabric care products that impart a sufficient fragrance level to the fabric, and, in some embodiments, release the fragrance when the fabric is ironed.

Introduction of a fragrance into a fabric care product is restricted by considerations such as availability and cost, and also by an inability of the fragrance to sufficiently deposit onto a fabric, and then remain on the fabric during the wash, rinse, and drying cycles. For example, a substantial amount of the fragrance deposited on a fabric is removed from the fabric during the drying process, even when the treated fabrics are line dried. It also has been demonstrated that a substantial amount of the fragrance in currently available fabric care products is lost during rinse cycles. This fragrance loss is attributed to the water solubility of various fragrance ingredients, to the volatility of fragrance ingredients that deposit on the fabric, and the wash-off of the fragrance from the fabric.

Typical fabric care products, such as laundry detergent compositions and fabric softener compositions, contain about 0.1% to about 1%, by weight, of a fragrance. U.S. Pat. No. 6,051,540 discloses that in the course of the washing clothes with a standard powdered laundry detergent, or a fabric softener rinse, only a small fraction of the fragrance present in these fabric care products is actually transferred to the fabric, i.e., as low as 1% of the original amount of fragrance present in these products.

Attempts have been made to increase fragrance deposition onto fabric, and to hinder or delay the release of the fragrance from the fabric, such that the laundered fabric remains esthetically pleasing for an extended length of time. One approach uses a carrier to introduce the fragrance to the fabric. The carrier is formulated to contain a fragrance and to adhere to the fabric during a washing cycle through particle entrainment or chemical change.

Fragrances have been adsorbed onto various materials, such as silica and clay, for delivery of the fragrance from detergents and fabric softeners to fabrics. U.S. Pat. No. 4,954,285 discloses fragrance particles especially for use with dryer-released fabric softening/antistatic agents. The fragrance particles are formed by adsorbing the fragrance onto silica particles having a diameter of greater than about one micron. The fragrance particles are included in dryer-activated solid fabric softener compositions including coated particles of fabric softener. The compositions release softener to fabrics in the dryer, and the fragrance particles improve the esthetic character of the fabric softener deposited on the fabric. The fragrance particles also can be admixed with detergent granules and can be coated or uncoated. This system has a drawback in that the fragrance is not sufficiently protected, and frequently is lost or destabilized during processing.

Another problem often associated with perfumed fabric care products is excessive odor intensity. A need therefore exists for a fragrance delivery system that provides satisfactory fragrance both during use and from the dry laundered fabric, and also provides prolonged storage benefits and an acceptable odor intensity of the fabric care product.

U.S. Pat. No. 6,790,814 discloses that a fragrance loaded into a porous carrier, such as zeolite particles, can be effectively protected from premature release of the fragrance by coating the loaded carrier particles with a hydrophobic oil, then encapsulating the resulting carrier particles with a water-soluble or water-dispersible, but oil-insoluble, material, such as a starch or modified starch.

U.S. Pat. Nos. 4,946,624; 5,112,688; and 5,126,061 disclose microcapsules prepared by a coacervation process. The microcapsules have a complex structure, with a large central core of encapsulated material, preferably a fragrance, and walls that contain small wall inclusion particles of either the core material or another material that can be activated to disrupt the wall. The microcapsules are incorporated into a fabric softener composition having a pH of about 7 or less and which further contains a cationic fabric softener. The encapsulated fragrance preferably is free of large amounts of water-soluble ingredients. The microcapsules are added separately to the fabric softener compositions. Ingredients that have high and low volatilities, compared to desired fragrance, either can be added to or removed from the fragrance to achieve the desired volatility. This type of controlled release system cannot be used with all types of fragrance ingredients, in particular, with fragrance ingredients that are relatively water soluble and/or are incapable of depositing onto a fabric.

U.S. Pat. No. 4,402,856 discloses a coacervation technique to provide fragrance particles for fabric care products containing gelatin or a mixture of gelatin with gum arabic, carboxymethylcellulose, and/or anionic polymers. The gelatin is hardened with a natural and/or synthetic tanning agent and a carbonyl compound. The particles adhere to the fabric during rinse cycles, and are carried over to the dryer. Diffusion of the fragrance from the capsules occurs only in the heat-elevated conditions of a dryer.

U.S. Pat. No. 4,152,272 discloses incorporating a fragrance into wax particles to protect the fragrance during storage and through the laundry process. The fragrance/wax particles are incorporated into an aqueous fabric conditioner composition. The fragrance diffuses from the particles onto the fabric in the heat-elevated conditions of the dryer.

U.S. Pat. Nos. 4,446,032 and 4,464,271 disclose liquid or solid fabric softener compositions comprising microencapsulated fragrance suspensions. The compositions contain sustained release fragrances prepared by combining nonconfined fragrance oils with encapsulated or physically entrapped fragrance oils. These combinations are designed such that the nonconfined fragrance oil is bound in a network of physically entrapped fragrance oil and suspending agent. The controlled release system comprises a mixture of (i) a nonconfined fragrance composition, (ii) one or more fragrance oils which are physically entrapped in one or more types of solid particles, and (iii) a suspending agent such as hydroxypropyl cellulose, silica, xanthan gum, ethyl cellulose, or combinations thereof. The nonconfined fragrance, the entrapped fragrance, and the suspending agent are premixed prior to preparation of the liquid or solid fabric softener compositions.

U.S. Pat. Nos. 4,973,422 and 5,137,646 disclose fragrance particles for use in cleaning and conditioning compositions. The particles comprise a fragrance dispersed within a wax material. The particles further can be coated with a material that renders the particles more substantive to the surface being treated, for example, a fabric in a laundry process. Such materials help deliver the particles to the fabric and maximize fragrance release directly on the fabric. In general, the coating materials are water-insoluble cationic materials.

U.S. Pat. No. 6,024,943 discloses particles containing absorbed liquids and methods of making the particles. A fragrance is absorbed within organic polymer particles, which further have a polymer at their exterior. The external polymer has free hydroxyl groups, which promote deposition of the particles from a wash or rinse liquor. The external polymer can be a component of an encapsulating shell, but typically is used as a stabilizer during polymerization of the particles. A highly hydrolyzed polyvinyl alcohol is a preferred external polymer.

U.S. Pat. No. 6,740,631 discloses a free-flowing powder formed from solid hydrophobic, positively-charged nanospheres containing an active ingredient, such as a fragrance, encapsulated in a moisture sensitive microsphere. To maximize deposition of the nanospheres on a fabric, particle size is optimized to ensure entrainment of the particles within the fabric fibers, and a sufficiently high cationic charge density on the particle surface is provided to maximize an ionic interaction between the particles and the fabric.

U.S. Pat. No. 7,119,057 discloses a polymeric encapsulated fragrance where the fragrance encapsulating polymer is coated with one cationic polymer. The cationic polymer aids in the deposition and stability of the polymeric encapsulated fragrance. The load of the cationic polymer is preferably from about 10% to about 500% of the fragrance containing composition, based on a ratio with the fragrance on a dry basis.

U.S. Pat. No. 7,119,060 discloses solid spheres comprising a crystallized waxy material. The waxy material may have a fragrance or other active agent incorporated therein, together with a cationic, hydrophobic charge-enhancing agent and a cationic softening agent. The spheres adhere to a fabric because of the cationic charge, and when ironing a dried fabric, a burst of fragrance occurs. The load of fragrance or other active agent is limited to about 30%, by weight, of the waxy material.

U.S. patent application Ser. No. 11/231,082 discloses the delivery of a benefit agent that is introduced into a formulation after admixture with a carrier. The agent and carrier composition requires a viscosity of at least 400 cps.

Generally, the prior art does not sufficiently teach or suggest a composition having a microparticulate material coated with one or more layers of two different cationic polymers for increased deposition of the microparticulate onto a substrate, such as a fabric. Moreover, the prior art does not teach or suggest a methodology for making a microparticulate material containing a benefit agent, such as a fragrance, coated with layers of two different cationic polymers.

SUMMARY OF THE INVENTION

The present disclosure relates to compositions comprising a cationically surface-modified microparticulate material, containing at least one benefit agent. Benefit agents include flavors, fragrances, insect repellents, silicone oils, fabric softening agents, anti-static agents, anti-wrinkle agents, stain-resistant agents, emollients, moisturizing agents, waxes, ultraviolet (UV) ray absorbers, antimicrobial agents, antioxidants, pigments, film-forming agents, skin-care agents, hair-care agents, scalp-care agents, anti-dandruff agents, hair-coloring agents, hair-conditioning agents, and the like. The cationic surface modification comprises two different cationic coating materials which increase the deposition and retention of the benefit agent-containing microparticulate material on a substrate, for example fabric, hair, skin, teeth, and hard surfaces. The disclosed compositions can further include additives, for example water, organic solvents, and surfactants, to formulate commercial products. Examples of compositions employing the disclosed benefit agent-containing microparticulate materials having a plurality of deposition-enhancing cationic coating materials include cleansing products, such as shampoos, conditioners, body washes, moisturizing agents, creams, shower gels, soaps, detergents, toothpastes, surface cleansing agents, and surface-conditioning agents, such as fabric softeners.

The microparticulate material can be a mixture of the benefit agent and a carrier agent or can be entirely composed of one or more benefit agents. One example is a microparticulate that is a porous solid carrier loaded with a benefit agent. The carrier can be a polymer (including film-forming polymers, phase-separated or coacervated polymers, and water-insoluble polymers, copolymers, and cross-polymers), wax, water-insoluble organic solid or liquid, and/or water-insoluble inorganic solid. Additionally, the microparticulates can be emulsion droplets formed, for example, from one or more benefit agents dispersed in two immiscible liquids. The microparticulate can further be a mixture of a benefit agent and a clay, such as a smectite clay, an organoclay, a water-insoluble inorganic microparticulate solid, hydrophilic liquid, hydrophobic liquid, gel, gum, solid including hydrocarbon solid, ester and/or ether solvent, silicone fluid, elastomer, wax, polymer, and/or mixtures, or the like.

The present disclosure additionally relates to the cationic surface modification of the microparticulate with two different polymers, a Type-1 Polymer and a Type-2 Polymer. The Type-1 Polymer is a polymer having a cationic atom content in the range of about 3 to about 20 wt. % and a weight average molecular weight in the range of about 300,000 to 800,000 Dalton. The Type-2 Polymer is a polymer having a cationic atom content of about 0.1 to about 3 wt. % and a weight average molecular weight greater than about 1,000,000 Dalton.

Importantly, the present improved characteristics of the disclosed composition are not obtained if the microparticulate is coated with only the Type-1 Polymer or coated with only the Type-2 Polymer, if the microparticulate is only coated with less than about 10%, more often less than about 60% of the Type-2 Polymer, or if the microparticulate is coated with two polymers where one or both do not meet weight average molecular weight and/or cationic atom content requirements.

The herein disclosed compositions and methods provide compositions with improved characteristics and use much lower amounts of cationic polymer(s) than previously employed in the prior art, making the disclosed compositions more commercially and industrially applicable. One important aspect of compositions that employ significantly lower amounts of cationic polymer(s) is that the resulting compositions can have a much higher concentration of benefit agent(s). Raising the concentration of the benefit agent in benefit agent containing compositions, with the herein defined improved characteristics, decreases the costs and formulation problems associated with the inclusion of benefit agent containing compositions in commercial products. The improved characteristics of the disclosed composition include stability against strong coagulation, enhanced deposition, and enhanced retention on a substrate. Herein, strong coagulation means the average particle size in a dispersion of agglomerated particles is at least three times greater than the average particle size in a dispersion of unagglomerated particle. Additional scope and description can be found below.

DETAILED DESCRIPTION OF THE PREFERRED EMBODIMENTS

The compositions and methods described herein have microparticulates as an integral component. As used herein, microparticulates are a plurality of different types of individual particulates having an average particle diameter that varies from about one to about 500 µm, preferably from about three to about 100 µm, more preferably from about six to about 50 µm, and still more preferably from about eight to about ten microns. Herein, microparticulates have at least one benefit agent. Microparticulates can be entirely made of one or more benefit agents or can be combinations of benefit agent(s) and particulate carrier(s).

Benefit agents are those compositions, chemicals, and formulations that impart a desired effect on a substrate whether the benefit agent or substrate is solid, liquid, gas, or combination. Examples of substrates include teeth, hair, skin, fabric, plastic, polymer, glass, metal, insects, plants, fungus, yeast, foods, drinks, and the like. A benefit agent can itself be a solid, liquid, gas, or mixture. Benefit agents include volatile and non-volatile compounds and/or compositions. Examples of volatile compounds include fragrances, insect repellants, therapeutic agents, and the like.

Suitable fragrances include but are not limited to fruits such as almond, apple, cherry, grape, pear, pineapple, orange, strawberry, raspberry, musk, and flower scents such as lavender-like, rose-like, iris-like, and carnation-like. Other fragrances include herbal scents such as rosemary, thyme, and sage; and woodland scents derived from pine, spruce and other forest smells. Fragrances may also be derived from various oils, such as essential oils, or from plant materials such as peppermint, spearmint and the like. Fragrances can be familiar and popular smells such as baby powder, popcorn, pizza, cotton candy and the like. Applicable fragrances can be found in U.S. Pat. Nos. 4,534,891, 5,112,688, 5,145,842, 6,844,302 and *Perfumes Cosmetics and Soaps*, Second Edition, edited by W. A. Poucher, 1959, all hereby incorporated by reference. The fragrances included in these references include acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

Applicable insect repellant benefit agents include dichlorvos, pyrethrin, allethrin, naled and/or fenthion pesticides disclosed in the U.S. Pat. No. 4,664,064, incorporated herein by reference. Preferable insect repellants are citronellal (3,7-dimethyl-6-octanal), N,N-diethyl-3-methylbenzamide (DEET), vanillin, and the volatile oils extracted from turmeric (*Curcuma longa*), kaffir lime (*Citrus hystrix*), citronella grass (*Cymbopogon winterianus*) and hairy basil (*Ocimum americanum*). Moreover, applicable insect repellants can be mixtures of insect repellants.

Examples of therapeutic benefit agents include creams or lotions, pharmaceuticals, neutraceuticals, homeopathic agents, and/or other materials.

Examples of non-volatile benefit agents include silicone oils, resins, and modifications thereof such as linear and/or cyclic polydimethylsiloxanes, amino-modified, alkyl, aryl, and alkylaryl silicone oils, which preferably have a viscosity greater than about 50,000 centistokes; organic and inorganic sunscreen actives, for example, octylmethoxy cinnamate; antimicrobial agents, for example, 2-hydroxy-2,4,4-trichlorodiphenylether; ester solvents, for example, isopropyl myristate; lipids and lipid like substance, for example, cholesterol; hydrocarbons such as paraffins, petrolatum, and mineral oil; fish and vegetable oils; hydrophobic plant extracts; therapeutic and skin-care reagents, for example, salicylic acid, benzoyl peroxide, and retinol; various waxes and soft solids; organic and inorganic fabric softening agents; and pigments including inorganic compounds with hydrophobically modified surface and/or dispersed in an oil or a hydrophobic liquid.

Particulate carriers include those materials for encapsulating a benefit agent. Particulate carriers can be porous polymeric or solid state materials, encapsulating shells, and the like. Examples of encapsulated benefit agents include those described in U.S. patent application Ser. No. 10/823,033, incorporated herein by reference, where the fragrances were encapsulated in substituted or un-substituted acrylic acid polymer or copolymer cross-linked with a melamine-formaldehyde pre-condensate or a urea-formaldehyde pre-condensate.

Examples of porous particulate carriers for holding benefit agents include various adsorbent polymeric microparticles available from AMCOL Int'l Corp., as noted below. One class of adsorbent polymeric microparticles is prepared by suspension polymerization techniques, as set forth in U.S. Pat. Nos. 5,677,407; 5,712,358; 5,777,054; 5,830,967; 5,834,577; 5,955,552; and 6,107,429, each incorporated herein by reference (available commercially under the tradename of POLY-PORE® E200, INCI name, ally methacrylates crosspolymer, from AMCOL Int'l, Arlington Heights, Ill.).

Another class of adsorbent polymeric microparticle is prepared by a precipitation polymerization technique, as set forth in U.S. Pat. Nos. 5,830,960; 5,837,790; 6,248,849; and 6,387,995, each incorporated herein by reference (available commercially under the trade name of POLY-PORE® L200 from AMCOL Int'l).

Yet another class of adsorbent polymeric microparticle is prepared by a precipitation polymerization technique as disclosed in U.S. Pat. Nos. 4,962,170; 4,948,818; and 4,962,133, each incorporated herein by reference. Examples of this class of absorbent polymeric microparticle are available commercially under the trade name of POLYTRAP by AMCOL Int'l (INCI name of lauryl methacrylate/glycol dimethacrylate cross polymer).

Additional adsorbent polymeric microparticles have been developed, for example those disclosed in U.S. Pat. No. Re. 33,429, incorporated herein by reference, and sold under the trade name of MACROBEAD by AMCOL Int'l (INCI name of lauryl methacrylate/glycol dimethacrylate cross polymer). Other adsorbent polymeric microparticles that are commercially available include, for example, MICROSPONGE® (INCI name of methyl methacrylate/glycol dimethylacrylate crosspolymer), as disclosed in U.S. Pat. No. 4,690,825, incorporated herein by reference, available from AMCOL Int'l, and the Poly-HIPE polymer (e.g., a copolymer of 2-ethylhexyl acrylate, styrene, and divinylbenzene) available from BIOPORE Corp., Mountain View, Calif.

In an other embodiment, particulate carriers include combinations of porous polymeric or solid state materials, encapsulating shells, absorbent polymeric microparticles, adsorbent polymers, and the like. One example of a microparticulate having a plurality of particulate carriers is an absorbent polymeric microparticle including a benefit agent and within an encapsulating shell.

The amount of the particulate carrier may range from about 10% to about 99% by weight of the microparticulate. One or more of the foregoing benefit agents is included in the compositions described herein in an amount varying from about 0.01 to about 80%, preferably from about 0.1 to about 40%, and most preferably from about 0.5 to about 20% of the total weight of the composition.

Methods for the general encapsulation of fragrances is known in the art, see for example U.S. Pat. Nos. 2,800,457, 3,870,542, 3,516,941, 3,415,758, 3,041,288, 5,112,688, 6,329,057, and 6,261,483, each incorporated herein by reference. Preferred encapsulating polymers include those formed from melamine-formaldehyde or urea-formaldehyde condensates, as well as similar types of aminoplasts. Additionally, capsules made by the simple or complex coacervation of gelatin are also preferred for use with the coating. Capsules having shell walls comprised of polyurethane, polyamide, polyolefin, polysaccaharide, protein, silicone, lipid, modified cellulose, gums, polyacrylate, polyphosphazines, polystyrene, and polyesters or combinations of these materials are also applicable.

Although many variations of materials and process steps are possible, representative methods used for aminoplast encapsulation and gelatin encapsulation are disclosed in U.S. Pat. Nos. 3,516,941 and 2,800,457, respectively, each incorporated herein by reference. Both of these processes are discussed in the context of fragrance encapsulation and for use in consumer products in U.S. Pat. Nos. 4,145,184 and 5,112,688, respectively, each incorporated herein by reference.

Preferably, the microparticulate has a neutral or anionic surface charge. The surface charge on the microparticulate can often be determined by a measurement of the zeta ($\zeta$)-potential and/or electrophoretic mobility. When the microparticulate has a neutral or cationic surface charge the microparticulate is often treated with an anionic polymer.

According to one embodiment of the cationically surface-modified benefit agent-containing microparticulate materials and methods described herein, the microparticulate material may be surface-treated with an anionic polymer or an anionic surfactant or mixtures thereof (herein termed anionic treatment agents), prior to the claimed surface-modification. The resulting anionic microparticulate material has approximately one monolayer of the anionic polymer and/or surfactant on the surface and is subsequently further surface-treated as described below for achieving the claimed cationic surface-modification. In this case, the anionic polymer and cationic polymer are not pre-mixed in the solution phase prior to adding to the microparticulate. Importantly, the anionic polymer and/or surfactant on the surface of the microparticulate is coated with the cationic polymer(s) disclosed herein and is neither entangled nor quaternized with the cationic polymer coating. The required amount of an anionic polymer or surfactant that may be used for the aforementioned anionic pre-treatment of the microparticulate material is such that the anionic surface charge resulting from the pre-treatment is relatively low, wherein the $\zeta$-potential of the microparticulate material in a dilute, approximately 0.1 wt. %, aqueous dispersion is preferably less than about −50 mV, while the conductivity of the dispersion is in the range of about 0.01 to about 0.5 mS/cm.

Applicable anionic polymers include water-soluble anionic polymers and water-insoluble anionic polymers. By way of non-limiting example, applicable water-soluble anionic polymers include polyphosphate, polysulfonates (e.g., polyvinyl sulfonate, lignosulfonates), polycarboxylates (e.g. sodium polyacrylate), polysulfates (e.g., polyvinyl sulfate), and silicone polymers with a pendant anionic group selected from carboxylate, sulfate, and phosphate groups. One example of a water-insoluble anionic polymer is the copolymer of castor oil phosphate and 3-isocyanato-methyl-3,5,5-trimethyl cyclohexyl isocyanate, referred to herein as castor oil phosphate/IPDI copolymer.

An important aspect of the microparticulate materials and methods described herein is the coating of the benefit agent-containing microparticulate material with two different cationic polymers. As used herein, coating means the polymer deposits onto the surface of the microparticulate and is not incorporated into the core of the microparticulate. Effectively, coating means the creation of an encapsulating layer of cationic polymer. This is distinct and significantly different from the entanglement or quaterization of a cationic polymer and an anionic polymer forming a particulate, known in the art, therein the particulate is not coated with the cationic polymer but encompasses the cationic polymer. Herein, these polymers are termed Type-1 Polymer and Type-2 Polymer. The Type-1 Polymer can be a homopolymer or a copolymer including an amphiphilic polymer or copolymer, a hydrophobically-modified polymer or copolymer, and the like. The preferred Type-1 cationic polymer is poly(diallyldimethyl ammonium halide), poly(DADMAC). The Type-2 Polymer can be a cationic guar gum, a cationic cellulose, a cationic starch, a hydrophobically-modified thereof, or the like.

Type-1 Polymers are selected from the cationic polymers that have a high cationic charge content. As used herein a high cationic charge content is measured by the cationic atom content. The cationic atom content is a measure of the total atomic weight of the atoms bearing cationic charge in/on the polymer chain divided by the molecular weight of the polymer, times 100, expressed as a weight percentage. By way of descriptive example, all of the cationic nitrogen atoms in the polymer poly(DADMAC) are quaternary ammonium ions, thereby the cationic atom content (here, the cationic nitrogen content) can be determined either by elemental analysis of a sample of the poly(DADMAC) or by the weight average molecular weight of the polymer. The elemental analysis would provide the weight percentage of nitrogen atoms in a sample of polymer, that is the cationic atom content. Preferably, a Type-1 Polymer has a cationic atom content in the range of about 3 wt. % to about 20 wt. %. More preferably, a Type-1 Polymer has a cationic atom content in the range of about 5 to about 15 wt. %, and still more preferably this polymer has a cationic atom content in the range of about 8 wt. % to about 10 wt. %. Even more preferably, a Type-1 Polymer has a cationic nitrogen content of at least 3 wt. %. Additionally, Type-1 Polymers, preferably, have a weight average molecular weight in the range of about 300,000 to about 800,000 Dalton, more preferably in the range of about 350,000 to about 600,000 Dalton, and still more preferably in the range of about 400,000 to about 550,000 Dalton.

The preferred Type-1 Polymer should have a solubility of less than 2 wt. % in a solution of anionic surfactant(s) containing 3 wt. % of an anionic surfactant. More preferably, the solubility of the Type-1 Polymer is less than about 1 wt. %, and even more preferably the solubility is less than about 0.5 wt. % in a 3 wt. % solution of an anionic surfactant, e.g., sodium laurylsulfate.

The preferred Type-1 Polymer is poly(diallyl dimethyl ammonium chloride), referred to herein as Poly(DADMAC), that has a cationic nitrogen content of about 8.7 wt. %. Other useful Type-1 Polymers include polyacrylates and polyolefins with pendant quaternary ammonium groups. For example, polymers that meet the above referenced weight average molecular weight, solubility, and cationic nitrogen content and also having the following compositions: polyquaternium 1 (CAS#: 68518-54-7); polyquaternium-2 (CAS#: 63451-27-1); polyquaternium-4 (copolymer of hydroxyethylcellulose and diallyldimethyl ammonium chloride); polyquaternium-5 (CAS#: 26006-22-4); polyquatemium-6 (polyallyldimethylammonium chloride (CAS#: 26062-79-3); polyquatemium-7 (CAS#: 26590-05-6); polyquaternium-8 (poly((methyl, stearyl) dimethylaminoethyl methacrylate), polyquatemium-9 (polydimethylaminoethylmethacrylate bromide); polyquaternium-10 (CAS#s: 53568-66-4, 55353-19-0, 54351-50-7, 81859-24-7; 68610-92-4, 81859-24-7); polyquatemium-11 (polyvinyl-N-ethylmethylpyrrolidonium); poly(ethyldimethylammonium ethylmethacrylate) sulfate copolymer), polyquaternium-12 (CAS#: 68877-50-9); polyquatemium-13 (CAS#: 68877-47-4); polyquatemium-14 (CAS#: 27103-90-8); polyquatemium-15 (CAS#: 35429-19-7); polyquatemium-16 (quaternary ammonium salt of methyl-vinylimidazolium chloride and vinylpyrrolidone) (CAS#: 95144-24-4); polyquatemium-17 (adipic acid-dimethylaminopropylamine polymer (CAS#: 90624-75-2); polyquatemium-18 (azelaic acid, dimethylaminopropylamine, dicholorethylether polymer, CAS#: 113784-58-0); polyquatemium-19 (polyvinyl alcohol, 2,3-epoxypropylamine polymer (CAS#: 110736-85-1); polyquaternium-20 (polyvinyl octadecylether, 2,3-epoxypropylamine polymer (CAS#: 110736-86-2); polyquaternium-22 (CAS#: 53694-17-0); polyquatemium-24 (hydroxyethylcellulose, lauryl dimethylammonium epoxide polymer); polyquatemium-27 (copolymer of polyquaternium-2 and polyquaternium-17, CAS#: 131954-48-4); polyquatemium-28 (vinylpyrrolidone, dimethylaminopropylmethacrylamide copolymer, CAS#: 131954-48-8), polyquaternium-29 (chitosan, CAS#: 9012-76-4); propylene oxide polymer reacted with epichlorohydrin); polyquatemium-30 (methylmethacrylate, methyl(dimethylacetylammonium ethyl)acrylate copolymer, (CAS#: 147398-77-4); polyquaternium-33 (CAS#: 69418-26-4); poly(ethylene(dialkyl)ammonium) polymethacrylamidopropyltrimonium chloride (CAS#: 68039-13-4); and poly(2-acryloyloxyethyl)trimethylammonium) are applicable Type-1 Polymers.

Type-2 Polymers are the cationic polymers that have a moderate to low cationic charge content. As used herein a moderate to low cationic charge content is measured by the cationic atom content, as defined above. Preferably, a Type-2 Polymer has a cationic atom content less than about 3 wt. %. More preferably, the Type-2 Polymer has a cationic atom content in the range of about 0.01 wt. % to about 3 wt. %, still more preferably in the range of about 0.1 wt. % to about 2 wt. %, and even more preferably in the range of about 0.5 wt. % to about 1 wt. %. Additionally, Type-2 Polymers, preferably, have a weight average molecular weight in the range of about 1,000,000 to about 15,000,000 Dalton, more preferably in the range of about 1,000,000 to about 10,000,000 Dalton, and still more preferably in the range of about 1,000,000 to about 5,000,000 Dalton.

Some useful Type-2 Polymers are those cationic polymers disclosed in U.S. Pat. No. 7,119,057, incorporated herein by reference, though herein used in significantly lower weight percentages. Preferable Type-2 Polymers include cationic copolymers of acrylamide, and cationic derivatives of natural polymers such as cellulose ether polymers, guar gum, and starch. Preferred Type-2 Polymers are those cationic derivatives of guar, cellulose, and/or starch that satisfy the above defined weight average molecular weight, and cationic weight percentage.

Another aspect of the cationically-modified benefit agent-containing microparticulate materials, compositions and methods described herein is the relative amounts of the Type-1 Polymer and Type-2 Polymer, in specific weight ratios, that are coated onto the benefit agent-containing microparticulate. Generally, the ratio of the weight of the Type-1 Polymer to the weight of the Type-2 Polymer should be in the range of about 0.1 to about 100. Preferably the weight ratio of the Type-1 Polymer to the Type-2 Polymer should be in the range of about 1 to 20, more preferably in the range of about 2 to about 20, and even more preferably in the range of about 2 to about 10, and most preferably about 3 to about 7. As expressed as weight percentages, the weight percentage of the Type-1 Polymer to the combined weight of the Type-1 and Type-2 polymer is in the range of about 50 to less than 100 wt. %, preferably in the range of about 60 to about 95 wt. %, and more preferably in the range of about 70 to about 90 wt. %. Correspondingly, the weight percentage of the Type-2 Polymer to the combined weight of the Type-1 and Type-2 polymer is in the range of about one to about 50 wt. %, preferably in the range of about 5 to about 40 wt. %, and more preferably in the range of about 10 to about 30 wt. %.

Yet another aspect of the cationically-modified benefit agent-containing microparticulate materials, compositions and methods described herein is the addition of the Type-1 Polymer and Type-2 Polymer (the cationic polymers) to the microparticulate in a specific weight ratio, irrespective of other materials, water, solvents, or items in the composition. Generally, the ratio of the weight of the cationic polymers to the weight of the microparticulate is in the range of about 0.01 to about 10. Preferably the ratio is in the range of about 0.05 to about 5, more preferably in the range of about 0.1 to about 1, and most preferably about 0.1 to about 0.3.

Additionally, the Type-1 Polymer and Type-2 Polymer are combined with the microparticulate to form a composition where the weight percentage of the microparticulate in the coated microparticulate composition is in the range of about 1 to about 99.9 wt. %, preferably in the range of about 35 to about 99.5 wt. %, and more preferably in the range of about 50 to about 99.0 wt. %, irrespective of other materials, water, solvents, or items in the composition. In one preferred coated microparticulate composition, the weight percentage of the Type-1 Polymer in the total composition is in the range of about 5 to about 20 wt. % and the weight percentage of the Type-2 Polymer is in the range of about 0.1 to about 5 wt. %, irrespective of other materials, water, solvents, or items in the composition.

The cationically-modified benefit agent-containing microparticulate materials, compositions and methods described herein can be made by any of a plurality of methods. The first involves the admixing of the Type-1 Polymer with the benefit agent-containing microparticulate followed by the admixing of the product from the addition of the Type-1 Polymer to the microparticulate with the Type-2 Polymer. One embodiment of this method is the surface-modification, surface-treatment, or coating of the microparticulate with the Type-1 Polymer, then the surface-modification, surface-treatment, or coating with the Type-2 Polymer. It is believed that this method yields a composition having the Type-1 Polymer bound to the surface of the microparticulate and having the Type-2 Polymer bound to the Type-1 Polymer and/or any of the microparticulate's surface area that is not coated with the Type-1 Polymer. A second method involves the admixing of the Type-1 Polymer with the Type-2 Polymer followed by the admixing of this cationic polymer mixture with the benefit agent-containing microparticulate to coat the benefit agent-containing microparticulate with both cationic polymers simultaneously. It is believed that this method yields a composition having the Type-1 Polymer preferentially bound to the microparticulate surface and the Type-2 Polymer bound to the Type-1 Polymer, in a layered structure similar to the structure produced from the sequential addition of Type-1 then Type-2 Polymers. The higher concentration, higher cationic atom content, and lower molecular weight of the Type-1 Polymer theoretically allow the Type-1 Polymer to more rapidly (based on relative reaction rates) add to the anionic microparticulate; such that the Type-1 Polymer coats greater than 50% of the microparticulate's surface area, preferably greater than 70%, more preferably greater than 90, and even more preferably greater than 95% of the microparticulate's surface area. A third method involves the admixing of the Type-1 Polymer with the Type-2 Polymer, followed by the admixing of this cationic polymer mixture with the benefit agent-containing microparticulate to coat the benefit agent-containing microparticulate with both cationic polymers simultaneously, followed by the admixing of this coated microparticulate with additional Type-2 Polymer. It is believed that this method yields a composition having an outer coating layer that is greater than 95% Type-2 Polymer, theoretically this method assures that the outer coating layer is 100% Type-2 Polymer.

The surface-modification, surface-treatment, or coating of the microparticulate material may be carried out by repeatedly adding the microparticulate material, either in a powder-form (generally, with a moisture content of less than 30% by weight) or as an aqueous dispersion, to an aqueous solution or dispersion containing a cationic polymer, and subsequently shearing the resulting dispersion. Alternatively, the microparticulate material in a powder-form may be blended with a mixture of a Type-1 Polymer and a Type-2 Polymer, wherein the two cationic polymers are used, respectively, in a form selected from a powder, a solution, a dispersion, and/or mixtures thereof.

For a microparticulate material having an anionic surface charge prior to the cationic surface-modification, the surface-modification, surface-treatment, or coating of the benefit agent-containing microparticulate material with the Type-1 Polymer is preferably carried out by adding the benefit agent-containing microparticulate material to an aqueous solution/dispersion of the polymer under high-shear agitation. The required amount of the Type-1 Polymer is such that the anionic surface-charge of the microparticulate material is partially or fully neutralized by the cationic charge of the Type-1 Polymer, inasmuch as the net surface-charge of the modified microparticulate-surface is cationic, and is sufficiently high for preventing strong coagulation amongst or between the dispersed particles of the microparticulate material, due to what is known in the art as the electrical double layer repulsion between electrically charged particles in a dispersion.

For any microparticulate material having a given anionic surface charge prior to the claimed surface-modification, an optimum dosage (amount added to the microparticulate material) of the Type-1 cationic polymer may be determined by a two step process. First, by measuring the minimum dosage at which the $\zeta$-potential of the microparticulate material in a dilute aqueous dispersion (generally about 0.02 to about 0.1 wt. % of the microparticulate material in water) is greater than about 65 mV, preferably greater than about 70 mV, and more preferably greater than about 75 mV, while the conductivity of the dispersion is in the range of about 0.01 to about 0.5 mS/cm. And second, by measuring the minimum dosage at which the sample does not strongly coagulate in a dilute, 0.1 wt. %, aqueous dispersion as measured by particle size analysis. The optimum dosage is when both steps are satisfied.

Yet another aspect of the cationically-modified microparticulate materials, compositions and methods described herein is the incorporation of the cationically-modified benefit agent-containing microparticulate materials in commercial products. The cationically-modified benefit agent-containing microparticulate materials can be used in products such as shampoo, liquid soap, bodywash, laundry detergent, fabric softener, toothpaste, and antiseptic ointments. These commercial products that contain cationically-modified benefit agent-containing microparticulate materials can further include solvents and/or other ingredients for the coated cationically-modified microparticulates. Examples of solvents and/or added ingredients include fatty alcohols, opacifiers, pearlescers, viscosity modifiers, rheology modifiers, inorganic oxides, buffering or pH adjusting chemicals, foam-boosters, perfumes, dyes, coloring agents or pigments, herb extracts, preservatives, hydrotopes, enzymes, bleaches, fabric conditioners, optical brighteners, antioxidants, stabilizers, thickeners, dispersants, soil release agents, anti-wrinkle agents, polymers, chelants, anti-corrosion agents, teeth cleansing and whitening agents, polymers, copolymers, cross-polymers, smectite clays, silica, silicate minerals, and the like. Generally, these products employ surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, 4,424,134, each hereby incorporated by reference. Liquid dish detergents are described in U.S. Pat. Nos. 6,069, 122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562, each hereby incorporated by reference. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818, each hereby incorporated by reference. Shampoo and conditioners that can employ the present invention include U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090, 4,705,681, each hereby incorporated by reference.

Non-limiting examples of suitable anionic surfactants that can be combined with the herein described microparticulate composition are the sodium, ammonium, and mono-, di-, and tri-ethanolamine salts of alkyl sulfates, alkyl ether sulfates, alkaryl sulfonates, alkyl succinates, alkyl sulfosuccinate, N-alkoyl sarcosinates, alkyl phosphates, alkyl ether phosphates, alkyl ether carboxylates, and α-olefin sulfonates. The alkyl groups generally contain from 8 to 18 carbon atoms and may be unsaturated. The alkyl ether sulfates, alkyl ether phosphates, and alkyl ether carboxylates may contain from 1 to 10 ethylene oxide or propylene oxide units per molecule, and preferably contain 2 to 3 ethylene oxide units per molecule. Non-limiting examples of nonionic surfactants that can be combined with the herein described microparticulate composition include, but are not limited to, aliphatic, primary or secondary linear or branched chain alcohols or phenols with alkylene oxides, generally ethylene oxide and generally 6-30 ethylene oxide groups. Other suitable nonionic surfactants include mono- or di-alkyl alkanolamides, alkyl polyglucosides, and polyhydroxy fatty acid amides. Non-limiting examples of amphoteric surfactants that can be combined with the herein described microparticulate composition include alkyl amine oxides, alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates, and acyl glutamates wherein the alkyl and acyl groups have from 8 to 18 carbon atoms. Nonlimiting examples of suitable cationic surfactants that can be combined with the herein described microparticulate composition include water-soluble or water-dispersible or water-insoluble compounds containing at least one amine group which is preferably a quaternary amine group, and at least one hydrocarbon group which is preferably a long-chain hydrocarbon group. The hydrocarbon group may be hydroxylated and/or alkoxylated and may comprise ester- and/or amido- and/or aromatic-groups. The hydrocarbon group may be fully saturated or unsaturated. Generally, the surfactant is combined with the microparticulate composition in a range from about 1 to about 95%, preferably from about 2 to about 90%, and most preferably from 3 to 90% by weight of the total compositions.

Alternatively the microparticulate composition can be formed into a commercial product by admixing the microparticulate composition with a hydrophilic solvent. Suitable hydrophilic solvents include water, glycerol, ethanol, isopropanol, propylene glycol, butylene glycol, hexylene glycol, polyethylene glycol and mixtures thereof. Generally, the solvent is combined with the microparticulate composition in a range from about 0.1 to about 95%, preferably from 1 to 90%, and most preferably from 3 to 90% by weight of the total compositions.

Examples

The following examples will more fully illustrate the preferred embodiments within the scope of the present invention. These examples are solely for the purpose of illustration and are not to be construed as limitations of the present invention as many variations thereof are possible without departing from the purview and spirit of the compositions and methods described herein. As used in the examples, given polymer weight percentages in tables 1-6 correspond to the relative weight percentage of the polymer to the microparticulate, irrespective of other possibly materials, water, solvents, or items in the compositions.

The cationic surface-treatment of the microparticulate material may be carried out by adding the microparticulate material, either in a powder-form (with a moisture content of less than 30% by weight) or as an aqueous dispersion, to an aqueous solution or dispersion containing the Type-1 Polymer and then adding the Type-1 coated microparticulate material to a solution or dispersion containing the Type-2 Polymer, and respectively shearing the resulting dispersions. Alternatively, the microparticulate material in a powder-form may be blended with a mixture of a Type-1 Polymer and a Type-2 Polymer, wherein the two polymers are used, respectively, in a form selected from a powder, a solution or a dispersion, and mixtures thereof.

For a microparticulate material having an anionic surface charge prior to the claimed surface-modification, the adsorption of the Type-1 Polymer onto the surface of the microparticulate material (coating step) is preferably carried out by adding the microparticulate material to an aqueous solution/dispersion of the polymer under high-shear agitation.

The general procedure for the preparation of the cationically surface-treated microparticulates can be understood through the herein disclosed representative examples. Table 1 provides the general formulations, as weight percents of the entire composition, of a number of prepared samples. These samples can be prepared through the adaptation of the representative examples through augmentation of the amounts of reagents added. Example 3 was prepared as follows: 60 g of a poly(DADMAC) solution (Zetag 7122, also called Magnafloc LT-7992, available from Ciba Specialty Chemicals, with 20% active) and 60 g of deionized water were added to a suitable flask. The batch was mixed for 6 minutes at a mixing speed of 200 rpm using a caframo mixer fitted with a dispersion blade agitator. After increasing the speed to 1,000 rpm, 300 g of an aqueous dispersion of an encapsulated fragrance (BL-AWAY-478A from International Flavors & Fragrances, Inc. (IFF, Inc.) New York, N.Y., with 40% encapsulated solids, including a fragrance) was added to the batch. The mixing speed was increased to at least 1,500 rpm, once about half of the dispersion-amount was added to the batch. Then a 1 g aliquot of a 50% (w/w) solution of sodium hydroxide was added to the batch within one minute after the completion of addition of the above dispersion, while the batch remained under agitation at a mixing speed of 1,500 rpm. The batch was mixed for 30 minutes at 1,500 rpm, counted from the time of completion of addition of the foregoing dispersion. The above dosage of the poly(DADMAC) solution corresponds to 10% poly(DADMAC), based on the weight of encapsulated solids, including a fragrance.

Table 1 shows examples of compositions of microparticulates coated with Type-1 Polymer, specifically poly(DADMAC) as prepared in the above described example 3. These samples became the starting materials for those samples shown in Table 2.

TABLE 1

| Ex. | Weight Percent of Type-1 Polymer {poly(DADMAC)} | Microparticulate material |
|---|---|---|
| 1 | 5 | BL-AWAY-478A |
| 2 | 7.5 | BL-AWAY-478A |
| 3 | 10 | BL-AWAY-478A |
| 4 | 12.5 | BL-AWAY-478A |
| 5 | 15 | BL-AWAY-478A |

Example 7 was prepared as follows: to 124 g of the resulting dispersion from Example 3 was added 26 g of a 2.5% (w/w) solution of a cationic guar (Jaguar C-14S from Rhodia), Type-2 Polymer, in a suitable vessel. The resulting mixture was mixed at a mixing speed of 1,000 rpm for 2.5 minutes, using a caframo mixer fitted with a dispersion blade agitator. The mixing speed was then increased to 1,500 rpm, and the batch was mixed for an additional 27.5 minutes. The amount of Type-1 Polymer and Type-2 Polymer correspond to 10 wt. % and 1.8 wt. %, respectively, based on the weight of encapsulated solids, including a fragrance.

Table 2 shows examples of microparticulate compositions corresponding to the present disclosure. The samples were prepared from the samples shown in Table 1 as described in the procedure for Example 7, above. For the purpose of these examples three Type-2 Polymers were employed. These are Jaguar C-17 (INCI Name: Guar hydroxypropyltrimonium chloride; CAS: 65497-29-2) available from Rhodia Inc. Cranberry N.J.; Jaguar C-14S (INCI Name: Guar hydroxypropyltrimonium chloride; CAS: 65497-29-2) available from Rhodia Inc.; and Soft-Cat SL-30 (INCI Name: Polyquaternium-67) available from Dow Chemical Co., Midland, Mich.

TABLE 2

| Ex. | Weight Percent of Type-1 Polymer {poly(DADMAC)} | Weight Percent of Type-2 Polymer | Name of Type-2 Polymer | | Microparticulate material |
|---|---|---|---|---|---|
| 6 | 10 | 1.8 | Jaguar C-17 | ex. 3 + type 2 | BL-AWAY-478A |
| 7 | 10 | 1.8 | Jaguar C-14S | ex. 3 + type 2 | BL-AWAY-478A |
| 8 | 10 | 1.8 | Soft-Cat SL-30 | ex. 3 + type 2 | BL-AWAY-478A |
| 9 | 12.5 | 1.8 | Jaguar C-17 | ex. 4 + type 2 | BL-AWAY-478A |
| 10 | 12.5 | 1.8 | Jaguar C-14S | ex. 4 + type 2 | BL-AWAY-478A |
| 11 | 12.5 | 1.8 | Soft-Cat SL-30 | ex. 4 + type 2 | BL-AWAY-478A |
| 12 | 15 | 1.8 | Jaguar C-17 | ex. 5 + type 2 | BL-AWAY-478A |
| 13 | 15 | 1.8 | Jaguar C-14S | ex. 5 + type 2 | BL-AWAY-478A |
| 14 | 15 | 1.8 | Soft-Cat SL-30 | ex. 5 + type 2 | BL-AWAY-478A |
| 15 | 10 | 3.8 | Jaguar C-17 | ex. 6 + type 2 | BL-AWAY-478A |
| 16 | 12.5 | 3.8 | Jaguar C-17 | ex. 9 + type 2 | BL-AWAY-478A |
| 17 | 15 | 3.8 | Jaguar C-17 | ex. 12 + type 2 | BL-AWAY-478A |
| 18 | 10 | 3.8 | Jaguar C-14S | ex. 7 + type 2 | BL-AWAY-478A |
| 19 | 12.5 | 3.8 | Jaguar C-14S | ex. 10 + type 2 | BL-AWAY-478A |
| 20 | 15 | 3.8 | Jaguar C-14S | ex. 13 + type 2 | BL-AWAY-478A |

Table 3 shows examples of microparticulate compositions corresponding to the present disclosures. Example 21 was prepared by the method described for example 3 but no NaOH solution was added to the dispersion. Examples 22, 23, and 24 were prepared as described for example 7 but example 21 was used as the precursor sample. Example 25 was prepared by the sequential treatment of the microparticulate material with the Type-1 Polymer and the Type-2 Polymer.

TABLE 3

| Ex. | Weight Percent of Type-1 Polymer {poly(DADMAC)} | Weight Percent of Type-2 Polymer | Name of Type-2 Polymer | | Microparticulate material |
|---|---|---|---|---|---|
| 21 | 15 | | | NaOH free | BL-AWAY-478A |
| 22 | 15 | 1.8 | Jaguar C-17 | ex. 21 + type 2 | BL-AWAY-478A |
| 23 | 15 | 3.8 | Jaguar C-17 | ex. 21 + type 2 | BL-AWAY-478A |
| 24 | 15 | 1.8 | Jaguar C-14S | ex. 21 + type 2 | BL-AWAY-478A |
| 25 | 10 | 1.8 | Jaguar C-17 | NaOH free | BL-AWAY-478A |

Table 4 shows examples of microparticulate compositions corresponding to the present disclosures. Example 26 was prepared by the method described for example 3 but no NaOH solution was added to the dispersion and SN-SBOO-1001AE from IFF, Inc., with 40% encapsulated solids, including a fragrance was used. Examples 27 and 28 were prepared as described for example 7 but example 26 was used at the precursor sample. Example 29 was prepared by the sequential treatment of the microparticulate material with the Type-1 Polymer and the Type-2 Polymer.

TABLE 4

| Ex. | Weight Percent of Type-1 Polymer {poly(DADMAC)} | Weight Percent of Type-2 Polymer | Name of Type-2 Polymer | | Microparticulate material |
|---|---|---|---|---|---|
| 26 | 15 | — | — | NaOH FREE | SN-SBOO-1001AE |
| 27 | 15 | 2.5 | Jaguar C-17 | ex. 26 + type 2 | SN-SBOO-1001AE |
| 28 | 15 | 1.8 | Jaguar C-17 | ex. 26 + type 2 | SN-SBOO-1001AE |
| 29 | 15 | 1.8 | Jaguar C-14S | NaOH free | SN-SBOO-1001AE |

Table 5 shows examples of microparticulate compositions corresponding to the present disclosures. Example 30 was prepared by the method described for example 3 but no NaOH solution was added to the dispersion and a galaxolide containing melamine capsule ("encapsulated galaxolide") dispersion from IFF, Inc., with 40% encapsulated solids, including the fragrance was used. Examples 31, 32, and 33 were prepared as described for example 7 but example 30 was used at the precursor sample. Example 34 was prepared by the method described for example 3 but an encapsulated galaxolide dispersion from IFF, Inc., with 40% encapsulated solids, including the fragrance was used. Examples 35, 36, and 37 were prepared as described for example 7 but example 34 was used at the precursor sample. Examples 38 and 39 were prepared by the sequential treatment of the microparticulate material with the Type-1 Polymer and the Type-2 Polymer without the addition of NaOH. Example 40 was prepared by the sequential treatment of the microparticulate material with the Type-1, then a NaOH solution, then the Type-2 polymer. Example 41 was prepared by the addition of the microparticulate material to a premixed sample of the Type-1 Polymer and the Type-2 Polymer. Example 42 was prepared by the subsequent addition of additional Type-2 polymer to the product of example 41.

Table 6 shows examples compositions comparing the ζ-potential and electrophoretic mobility of coated microparticulate materials. The results show the importance of the weight average molecular weight of the Type-1 Polymer; the comparison is between two different poly(DADMAC) polymers, a non-Type-1 Polymer: Zetag 7131 (Mw=75,000-125,000 Dalton) and a Type-1 Polymer: Zetag 7122 (Mw=400,000-450,000 Dalton), both from Ciba Specialty Chemicals. The sample with the Type-1 Polymer, that is the polymer that has a weight average molecular weight between about 300,000 and about 800,000 Dalton, shows significantly higher ζ-potential and electrophoretic mobility indicating higher charge on the microparticulate and very limited to no coagulation in a dispersion.

TABLE 6

| Ex. | Weight Percent of Polymer | Name of Polymer | Microparticulate material |
|---|---|---|---|
| 43 | 20 | Zetag 7131 | BL-AWAY-478A |
| 43A | 20 | Zetag 7122 | BL-AWAY-478A |

TABLE 5

| Ex. | Weight Percent of Type-1 Polymer {poly(DADMAC)} | Weight Percent of Type-2 Polymer | Name of Type-2 Polymer | | Microparticulate material |
|---|---|---|---|---|---|
| 30 | 15 | — | — | NaOH FREE | Encapsulated galaxolide |
| 31 | 15 | 1.8 | Jaguar C-17 | ex. 30 + type 2 | Encapsulated galaxolide |
| 32 | 15 | 3.8 | Jaguar C-17 | ex. 30 + type 2 | Encapsulated galaxolide |
| 33 | 15 | 1.8 | Jaguar C-14S | ex. 30 + type 2 | Encapsulated galaxolide |
| 34 | 15 | — | — | NaOH | Encapsulated galaxolide |
| 35 | 15 | 3.8 | Jaguar C-17 | ex. 34 + type 2 | Encapsulated galaxolide |
| 36 | 15 | 1.8 | Soft-Cat SL-30 | ex. 34 + type 2 | Encapsulated galaxolide |
| 37 | 15 | 3.8 | Jaguar C-14S | ex. 34 + type 2 | Encapsulated galaxolide |
| 38 | 10 | 1.8 | Jaguar C-14S | sequential treatment NaOH free | Encapsulated galaxolide |
| 39 | 10 | 1.8 | Jaguar C-17 | sequential treatment NaOH free | Encapsulated galaxolide |
| 40 | 10 | 3.8 | Jaguar C-14S | sequential treatment | Encapsulated galaxolide |
| 41 | 10 | 1.8 | Jaguar C-14S | Type 1 Type 2 Preblend | Encapsulated galaxolide |
| 42 | 10 | 3.8 | Jaguar C-14S | ex. 41 + C-14S | Encapsulated galaxolide |

TABLE 6-continued

| Ex. | Zeta-potential, mV | | Electrophoretic Mobility, μm/V⁻¹s⁻¹ | |
|---|---|---|---|---|
| 43 | | 58.35 | | 4.601 |
| | | 55.86 | | 4.404 |
| | | 57.24 | | 4.513 |
| | Mean: | 57.15 | Mean: | 4.506 |
| 43A | | 79.61 | | 6.277 |
| | | 78.00 | | 6.149 |
| | | 79.94 | | 6.303 |
| | Mean: | 79.18 | Mean: | 6.243 |

Table 7 shows examples of shower gel compositions employing the herein described microparticulate compositions.

TABLE 7

| Ingredients | Weight %, Shower Gel 1 | Weight %, Shower Gel 2 | Weight %, Shower Gel 3 | Weight %, Shower Gel 4 |
|---|---|---|---|---|
| Deionized Water | 35 | 35 | 33.5 | 33.5 |
| Ammonium Lauryl Sulfate (Stepanol AMV, 28% active, from Stepan Company) | 50 | 50 | 50 | 50 |
| Cocamidopropyl Betaine (Amphosol CG, 30% active, Stepan Company) | 12 | 12 | 12 | 12 |
| Composition of EXAMPLE 28 | 3 | | | |
| Composition of EXAMPLE 29 | | 3 | | |
| Composition of EXAMPLE 31 | | | 4.5 | |
| Composition of EXAMPLE 36 | | | | 4.5 |

Table 8 shows examples of shampoo compositions employing the herein described microparticulate compositions.

TABLE 8

| Ingredients | Weight %, Shampoo 1 | Weight %, Shampoo 2 | Weight %, Shampoo 3 | Weight %, Shampoo 4 |
|---|---|---|---|---|
| Deionized Water | 6.87 | 6.87 | 5.37 | 5.37 |
| Disodium Laureth Sulfosuccinate (Stepan-Mild SL3, 32.5% active, from Stepan Company) | 38 | 38 | 38 | 38 |
| Sodium Laureth Sulfate (Steol CS-330, 28.5% active, from Stepan Company) | 35 | 35 | 35 | 35 |
| Cocamidopropyl Betaine (Amphosol CG, 30% active, Stepan Company) | 16.5 | 16.5 | 16.5 | 16.5 |
| 50% Sodium Hydroxide | 0.63 | 0.63 | 0.63 | 0.63 |
| Composition of EXAMPLE 28 | 3 | | | |
| Composition of EXAMPLE 29 | | 3 | | |
| Composition of EXAMPLE 31 | | | 4.5 | |
| Composition of EXAMPLE 36 | | | | 4.5 |

What is claimed:

1. A coated microparticulate composition comprising a microparticulate having a particle size in the range of about 1 μm to about 500 μm, a Type-1 Polymer, and a Type-2 Polymer; wherein the microparticulate comprises a benefit agent comprising about 35 wt. % to about 99.5 wt. % of the coated microparticulate; and wherein the microparticulate is coated:
   first with the Type-1 Polymer, wherein the Type-1 Polymer comprises a cationic polymer with a cationic atom content of about 3 wt. % to about 20 wt. % and a weight average molecular weight of about 300,000 to about 800,000 Dalton; and
   then with the Type-2 Polymer, wherein the Type-2 Polymer comprises a cationic polymer with a cationic atom content of about 0.1 wt. % to about 3 wt. % and a weight average molecular weight greater than about 1,000,000 Dalton; wherein the weight ratio of the Type-1 Polymer to Type-2 Polymer is in the range of 3 to 7.

2. The coated microparticulate composition of claim 1, wherein the cationic atom content in both the Type-1 Polymer and the Type-2 Polymer comprise quaternary ammonium ions.

3. The coated microparticulate composition of claim 1 wherein the microparticulate is combined with an additive selected from the group consisting of water, an organic solvent, a surfactant, and a mixture thereof to form the microparticulate composition.

4. The coated microparticulate composition of claim 1, wherein the microparticulate has an average particle diameter of about 3 to about 100 microns.

5. The coated microparticulate composition of claim 4, wherein the microparticulate has an average particle diameter of about 6 to about 50 microns.

6. The coated microparticulate composition of claim 4, wherein the microparticulate has a diameter of about 8 to about 10 microns.

7. The coated microparticulate composition of claim 1, wherein the microparticulate is carried by a particulate carrier.

8. The coated microparticulate composition of claim 7, wherein the particulate carrier is selected from the group consisting of an adsorbent polymeric microparticle, an adsorbent polymer, a porous solid state material, a porous polymeric material, an encapsulating shell, and a mixture thereof.

9. The coated microparticulate composition of claim 1, wherein the benefit agent is selected from the group consisting of a flavor, a fragrance, an insect repellent, a silicone oil, a fabric softening agent, an anti-static agent, an anti-wrinkle agent, a stain-resistant agent, an emollient, a moisturizing agent, a wax, an ultraviolet (UV) ray absorber, an antimicrobial agent, an antioxidant, a pigment, a film-forming agent, a skin-care agent, a hair-care agent, a scalp-care agent, an anti-dandruff agent, a hair-coloring agent, a hair-conditioning agent, and a mixture thereof.

10. The coated microparticulate composition of claim 1, wherein the Type-1 Polymer has a weight average molecular weight of about 350,000 to about 600,000 Dalton.

11. The coated microparticulate composition of claim 10, wherein the Type-1 Polymer has a weight average molecular weight of about 400,000 to about 550,000 Dalton.

12. The coated microparticulate composition of claim 1, wherein the Type-1 Polymer has a cationic atom content in the range of about 5 wt. % to about 15 wt. %.

13. The coated microparticulate composition of claim 12, wherein the Type-1 Polymer has a cationic atom content of about 8 wt. % to about 10 wt. %.

14. The coated microparticulate composition of claim 1, wherein the Type-2 Polymer has a weight average molecular weight of about 1,000,000 to about 15,000,000 Dalton.

15. The coated microparticulate composition of claim 14, wherein the Type-2 Polymer has a weight average molecular weight of about 1,000,000 to about 10,000,000 Dalton.

16. The coated microparticulate composition of claim 15, wherein the Type-2 Polymer has a weight average molecular weight of about 1,000,000 to about 5,000,000 Dalton.

17. The coated microparticulate composition of claim 1, wherein the Type-2 Polymer has a cationic atom content in the range of about 0.1 wt. % to about 2 wt. %.

18. The coated microparticulate composition of claim 17, wherein the Type-2 Polymer has a cationic atom content in the range of about 0.5 wt. % to about 1 wt. %.

19. The composition of claim 1, wherein the coated microparticulate composition consists essentially of the microparticulate, a Type-1 Polymer, and a Type-2 Polymer.

20. The coated microparticulate composition of claim 1, wherein the microparticulate comprises about 50 wt. % to about 99.0 wt. % of the coated microparticulate composition.

21. The coated microparticulate composition of claim 20, wherein the microparticulate comprises about 65 wt. % to about 95.0 wt. % of the coated microparticulate composition.

22. A product selected from the group consisting of a shampoo, a conditioner, a body wash, a moisturizing agent, a cosmetic cream, a shower gel, a soap, a detergent, a toothpaste, a surface cleansing agent, a surface conditioning agent, and a mixture thereof, wherein the product comprises the coated microparticulate composition of claim 1.

23. A method of making a coated microparticulate composition consisting essentially of a microparticulate coated with a Type-1 Polymer and a Type-2 Polymer, wherein the microparticulate comprises a benefit agent comprising about 35 wt. % to about 99.5 wt. % of the coated microparticulate comprising:
admixing a sufficient amount of a Type-1 Polymer with a microparticulate to raise a ζ-potential of an aqueous dispersion of the admixed Type-1 Polymer and microparticulate to at least 65 mV when measured at a concentration of about 0.1 wt. % microparticulate in water; and admixing a Type-2 Polymer with the microparticulate, wherein the Type-1 Polymer has a cationic nitrogen content of at least about 3 wt. % and a weight average molecular weight of less than about 800,000 Dalton, wherein the Type-2 Polymer has a cationic nitrogen content of less than about 3 wt. % and a weight average molecular weight of greater than about 1,000,000 Dalton: and wherein the weight ratio of the Type-1 Polymer to Type-2 Polymer is in the range of 3 to 7.

24. The method of claim 23, wherein a ratio of the combined weight of the Type-1 Polymer and the Type-2 Polymer to the weight of the microparticulate is in the range of about 0.01 to about 10.

25. The method of claim 23, wherein the microparticulate is selected from the group consisting of a benefit agent, a particulate carrier, and a mixture thereof.

26. The method of claim 23, wherein the method comprises admixing the Type-1 Polymer with the microparticulate to form a Type-1 Polymer-coated microparticulate, and then admixing the Type-2 Polymer with the Type-1 Polymer coated microparticulate.

27. The method of claim 23, wherein the method comprises admixing the Type-1 Polymer with the Type-2 Polymer to make a polymer composition and then admixing the polymer composition with the microparticulate to form the coated microparticulate.

28. The method of claim 23, wherein the microparticulate prior to admixing with either the Type-1 Polymer or the Type-2 Polymer has a neutral or cationic surface charge, and further comprising admixing a sufficient amount of an anionic treatment agent selected from the group consisting of an anionic surfactant, an anionic polymer, and a mixture thereof, with the microparticulate to change the ζ-potential of an aqueous dispersion of the admixed anionic treatment agent and microparticulate to at least −50 mV when measured at a concentration of about 0.1 wt. % microparticulate in water.

29. A microparticulate coating composition consisting essentially of a polymer mixture, wherein the polymer mixture consists of a Type-1 Polymer and a Type-2 Polymer, and wherein the polymer mixture comprises about 50 wt. % to about 99 wt. % of the Type-1 Polymer and about 1 wt. % to about 50 wt. % of the Type-2 Polymer, based on the total weight of the polymers in the mixture, wherein the Type-1 Polymer has a cationic nitrogen content of at least about 3 wt. % and a weight average molecular weight of less than about 800,000 Dalton, wherein the Type-2 Polymer has a cationic nitrogen content of less than about 3 wt. % and a weight average molecular weight of greater than about 1,000,000 Dalton; and wherein the weight ratio of the Type-1 Polymer to Type-2 Polymer is in the range of 3 to 7.

30. The microparticulate coating composition of claim 29, wherein the polymer mixture comprises about 60 wt. % to about 95 wt. % of the Type-1 Polymer and about 5 wt. % to about 40 wt. % of the Type-2 Polymer, based on the total weight of the polymers in the mixture.

31. The microparticulate coating composition of claim 30, wherein the polymer mixture comprises about 70 wt. % to about 90 wt. % of the Type-1 Polymer and about 10 wt. % to about 30 wt. % of the Type-2 Polymer.

32. The microparticulate coating composition of claim 30, wherein the Type-1 Polymer is a poly(DADMAC) and wherein the Type-2 Polymer is selected from the group consisting of a cationically modified guar, a cationically modified cellulose, and a mixture thereof.

33. A method of applying a benefit agent to a substrate comprising contacting the substrate with a coated microparticulate consisting essentially of a microparticulate coated with a Type-1 Polymer and a Type-2 Polymer, wherein the microparticulate comprises a benefit agent comprising about 35 wt. % to about 99.5 wt. % of the coated microparticulate, and
rinsing the substrate with water;
wherein the coated microparticulate comprises a benefit agent or a carrier containing the benefit agent coated with the Type-1 Polymer and the Type-2 Polymer at a weight ratio of the Type-1 Polymer to Type-2 Polymer in the range of 3 to 7, wherein the Type-1 Polymer has a cationic nitrogen content of at least about 3 wt. % and has a weight average molecular weight of less than about 800,000 Dalton, and the Type-2 Polymer has a cationic nitrogen content in a range of about 0.1 wt. % to about 3 wt. % and having a weight average molecular weight of at least about 1,000,000 Dalton, and wherein the coated microparticulate has an increased deposition and an increased retention on the substrate as compared to a coated microparticulate having the same weight percentage microparticulate selected from the group consisting of a first microparticulate consisting essentially of a microparticulate coated with only a Type-1 Polymer; a second microparticulate consisting essentially of a microparticulate coated with only a Type-2 Polymer.

34. The method of claim 33, wherein the coated microparticulate about 5 wt. % to about 20 wt. % of the Type-1 Polymer based on the total weight of the coated microparticulate, and about 0.1 wt. % to about 5 wt. % of the Type-2 Polymer based on the total weight of the coated microparticulate.

* * * * *